United States Patent
Najafi et al.

(10) Patent No.: US 10,299,736 B2
(45) Date of Patent: May 28, 2019

(54) METHOD, DEVICE, AND SYSTEM FOR DIAGNOSING AND MONITORING FRAILTY

(71) Applicant: THE ARIZONA BOARD OF REGENTS ON BEHALF OF THE UNIVERSITY OF ARIZONA, Tucson, AZ (US)

(72) Inventors: Bijan Najafi, Tucson, AZ (US); Saman Parvaneh, Tucson, AZ (US); Martha Jane Mohler, Tucson, AZ (US); David G. Armstrong, Tucson, AZ (US); Mindy Joy Fain, Tucson, AZ (US); Marvin J. Slepian, Tucson, AZ (US)

(73) Assignee: THE ARIZONA BOARD OF REGENTS ON BEHALF OF THE UNIVERSITY OF ARIZONA, Tucson, AZ (US)

( * ) Notice: Subject to any disclaimer, the term of this patent is extended or adjusted under 35 U.S.C. 154(b) by 126 days.

(21) Appl. No.: 14/671,980

(22) Filed: Mar. 27, 2015

(65) Prior Publication Data
US 2015/0272511 A1   Oct. 1, 2015

Related U.S. Application Data

(60) Provisional application No. 61/971,153, filed on Mar. 27, 2014.

(51) Int. Cl.
*A61B 5/00* (2006.01)
*A61B 5/11* (2006.01)
(Continued)

(52) U.S. Cl.
CPC ........ *A61B 5/7275* (2013.01); *A61B 5/02405* (2013.01); *A61B 5/112* (2013.01);
(Continued)

(58) Field of Classification Search
None
See application file for complete search history.

(56) References Cited

U.S. PATENT DOCUMENTS

2009/0076364 A1\* 3/2009 Libbus ............... A61B 5/0002
600/391
2011/0208444 A1   8/2011 Solinsky
(Continued)

OTHER PUBLICATIONS

Fried, et al, "Untangling the concepts of disability, frailty, and comorbidity: implications for improved targeting and care" Journal of Gerontology: Medical Sciences, 2004, vol. 59, No. 3, 255-263 (9 pages total).
(Continued)

*Primary Examiner* — Christopher Koharski
*Assistant Examiner* — Elizabeth K So
(74) *Attorney, Agent, or Firm* — Stuart H. Mayer; Mayer & Williams PC

(57) ABSTRACT

Methods, devices, and systems according to present principles provide ways to diagnose frailty and assess the severity of its clinical status—e.g., non-frail, pre-frail, and frail, especially as measured and quantified during activities of daily living. Systems and methods according to present principles objectively quantify physical activity behaviors and identify specific motor tasks, which indicate clinical frailty syndrome behaviors such as flopping, cautious-sitting, non-uniform walking fluctuations, cognitive decline, slowness, weakness, and exhaustion. Additionally, the systems and methods allow improved sensitivity and specificity of frailty identification by further assessing physiological parameters such as heart rate, respiration rate, and skin temperature in response to, or recovery from, specific activities.

39 Claims, 10 Drawing Sheets

(51) Int. Cl.
*A61B 5/024* (2006.01)
*A61B 5/08* (2006.01)

(52) U.S. Cl.
CPC .......... *A61B 5/1118* (2013.01); *A61B 5/0002* (2013.01); *A61B 5/0816* (2013.01); *A61B 5/1116* (2013.01); *A61B 5/1123* (2013.01)

(56) References Cited

U.S. PATENT DOCUMENTS

| | | | | |
|---|---|---|---|---|
| 2011/0288811 | A1* | 11/2011 | Greene | A61B 5/1038 702/141 |
| 2013/0274587 | A1 | 10/2013 | Coza | |
| 2013/0338802 | A1 | 12/2013 | Winsper | |
| 2014/0243686 | A1* | 8/2014 | Kimmel | A61B 5/1118 600/476 |
| 2014/0336947 | A1 | 11/2014 | Walke | |
| 2015/0223743 | A1 | 8/2015 | Pathangay | |

OTHER PUBLICATIONS

G. Abellan Van Kan, et al. "The I.A.N.A. Task Force on Frailty Assessment of Older People in Clinical Practice" The Journal of Nutrition, Health & Aging© vol. 12, No. 1, 29-37, 2008 (9 pages total).

N.M. de Vries, et al. "Outcome instruments to measure frailty: A systematic review", Ageing Research Reviews 10 (2011) 104-114 (11 pages total).

Cooper R., Kuh D, Hardy R., "Objectively measured physical capability levels and mortality: systematic review and meta-analysis" BMJ 2010; 341:c4467 (12 pages total).

G. Abellan Van Kan, et al., "Gait Speed at Usual Pace as a Predictor of Adverse Outcomes in Community-Dwelling Older People an International Academy on Nutrition and Aging (IANA) Task Force" JThe Journal of Nutrition, Health & Aging© vol. 13, No. 10, 881-889 (10 pages total).

Moscato BS, et al., "Validation of a modified center for epidemiologic studies depression (CES-D) scale with a one-month time frame" American Journal of Epidemiology. 1998; 147(11): 218-218 (2 pages total).

Bijan Najafi, Ph.D., M.Sc., et al. "Novel Wearable Technology for Assessing Spontaneous Daily Physical Activity and Risk of Falling in Older Adults with Diabetes" Journal of Diabetes Science and Technology vol. 7, Issue 5, Sep. 2013, 1147-60 (14 pages total).

Farina, et al. "Assessment of Average Muscle Fiber Conduction Velocity From Surface EMG Signals During Fatiguing Dynamic Contractions", IEEE Transactions of Biomedical Engineering, vol. 51, No. 8, Aug. 2004.

Theou et al., "Daily Muscle activity and quiescence in non-frail, pre-fail, and frail older woman", Experimental Gerontology 45 (2010) 909-917.

Bigland-Ritchie et al. "Conduction Velocity and EMG power spectrum changes in fatigue of sustained maximal efforts", American Physiological Socity, 1981.

Polanczyk CA, Marcantonio E, Goldman L et al. Impact of age on perioperative complications and length of stay in patients undergoing noncardiac surgery. Ann Intern Med 2001; 134:637-643.

Makary MA, Segev DL, Pronovost PJ et al. Frailty as a predictor of surgical outcomes in older patients. J Am Coll Surg 2010; 210:901-908.

Davenport DL, Bowe EA, Henderson WG et al. National Surgical Quality Improvement Program (NSQIP) risk factors can be used to validate American Society of Anesthesiologists Physical Status classification (ASA PS) levels. Ann Surg 2006; 243:636-644.

Fried LP, Tangen CM, Walston J et al. Frailty in older adults: Evidence for a phenotype. J Gerontol A Biol Sci Med Sci 2001; 56A:M146-M156.

Rockwood K, Andrew M, Mitnitski A. A comparison of two approaches to measuring frailty in elderly people. J Gerontol A Biol Sci Med Sci 2007;62A:738-743.

Rockwood K, Song X, MacKnight C et al. A global clinical measure of fitness and frailty in elderly people. Can Med Assoc J 2005; 173:489-495.

Toosizadeh N, Mohler J, Najafi B. Assessing Upper Extremity Motion: An Innovative Method to Identify Frailty. JGS 2015; Manuscript No. 13451.

Kubicki A, Bonnetblanc F, Petrement G, Ballay Y, Mourey F. Delayed postural control during self-generated perturbations in the frail older adults. Clin Interv Aging. 2012; 7: 65-75.

Folstein MF, Folstein SE, McHugh PR. 'Mini-mental state'. A practical method for grading the cognitive state of patients for the clinician. J Psychiatr Res 1975; 12:189-198.

* cited by examiner

METHOD, DEVICE, AND SYSTEM FOR DIAGNOSING AND MONITORING FRAILTY

CROSS-REFERENCE TO RELATED APPLICATIONS

This application claims benefit of priority of US Provisional Patent Application Ser. No. 61/971,153, filed Mar. 27, 2014, entitled "METHOD, DEVICE, AND SYSTEM FOR DIAGNOSING AND MONITORING FRAILTY", owned by the owner of the present application and herein Incorporated by reference in its entirety.

STATEMENT OF FEDERAL FUNDING

This invention was made with government support under Grant No. R42 AG032748 awarded by NIH. The government has certain rights in the invention.

FIELD

This invention generally relates to body movement monitoring systems, and more particularly to systems which relate to measuring and evaluating frailty.

BACKGROUND

The geriatric syndrome of "frailty" is one of the greatest challenges facing our aging population, and is associated with adverse health outcomes, dependency, institutionalization and mortality. Frailty prevalence increases with age, with up to 30% of the population meeting frailty criteria by age 90. The US population of (frail) elders is rapidly growing, and health care utilization and associated costs among this population account for a disproportionate amount of US health care costs. In geriatric care, prevention, early diagnosis, intervention and management of frailty are critical and growing challenges.

Beyond the geriatric population, frailty as a clinical syndrome has also been observed in select younger patients. In particular, those with underlying chronic viral infections such as HIV have been found to be frail. Similarly, patients with chronic renal insufficiency on dialysis have been diagnosed as frail, as well as adult survivors of childhood cancers. Hence frailty is becoming increasingly recognized as a distinct clinical syndromic state, in a wide range of patients, over a wide range of ages.

Frailty syndrome (FS) or just 'frailty' is a clinically-recognized syndrome and phenotype in which an individual develops a reduced tolerance and capacity to deal with stressors. Frailty manifests as a limited capacity to maintain homeostasis and is characterized by a clinical state of age-related biological vulnerability to stressors and decreased physiological reserves with alterations in energy metabolism, decreased skeletal muscle mass and quality, and altered hormonal and inflammatory functions. FS is also associated with excess functional decline, dependency, increased healthcare utilization, hospitalization, institutionalization, and death.

An unmet need exists in developing devices, methods and systems to diagnose frailty, to determine its stages and severity, to monitor its status and/or change over time, and to differentiate it from other debilitating diseases or from simple age-related functional decline.

This Background is provided to introduce a brief context for the Summary and Detailed Description that follow. This Background is not intended to be an aid in determining the scope of the claimed subject matter nor be viewed as limiting the claimed subject matter to implementations that solve any or all of the disadvantages or problems presented above.

SUMMARY

Systems and methods, according to present principles, are directed towards an ambulatory system which in one implementation (1) measures and quantifies parameters related to the user's postures and movement; (2) evaluates the user's frailty status; and (3) evaluates various symptoms associated with aging, including cognitive decline and physiological response deficit. The systems and methods generally employ a movement or motion sensor, e.g., accelerometer, GPS sensor, or the like, along with an optional physiological sensor and/or audio sensor. The motion sensor allows classification of spontaneous daily physical activity, and may be implemented as part of a smart phone, smart watch, dedicated device, or other sensor, including wearable sensors. The optional sensors may be used to measure heart rate, respiration rate, skin temperature, and so on. As noted the sensors may be wearable, and may combine with a processor that performs a method detailed herein that allows identification of frailty status during activities of daily living.

The significance of the measurement and evaluation relates to the desire to focus therapeutic efforts accurately based upon a correct underlying condition. Accurate diagnosis of emergent frailty offers the potential for therapeutic intervention, which may alter the progression of this phenotype with hopes for a return towards normalcy or complete recovery.

Among others, systems and methods according to present principles may be associated with several fields.

For example, in the field of elderly care, physical therapy, inpatient care, and home tele-monitoring, systems and methods according to present principles find several important uses, including providing quantification of frailty status based on monitoring of an elderly person's physical activity (PA) during his or her everyday life. This information may be useful for several reasons: first, PA monitoring can accurately determine the user's state of frailty and healthy physiological and cognitive status. For example, the systems and method can detect early deteriorations in frailty and cognition due to various health conditions, e.g. development of infections, medication side effects, loss of muscle mass, inappropriate diet, etc. Second, PA monitoring provides valuable information about responses to interventions, e.g. exercise, diet, medication, etc. Third, PA monitoring can evaluate the risk of complication to an intervention, e.g., whether the user can support a surgical intervention, etc. This information may significantly aid clinicians to tailor and personalize the type of intervention based on the frailty status of the user. Fourth, monitoring of frailty status can be used to identify risk of falling of the user. This information may further aid health care providers in the optimization of logistics and attention required for the user. Fifth, assessment of the effects of new drugs, pain treatments, new rehabilitation, and diet are significantly advanced through monitoring of the subject's frailty status through the monitoring of the user's physical activity and other user parameters during his or her everyday life. Systems and methods according to present principles may also find use in remote monitoring and tele-care of people suffering from various diseases, such as Alzheimer's, cognitive impairment, arthritis, stroke, etc., as well as of those recovering and rehabilitating from diseases, accidents, and medical procedures.

In the field of clinical research and studies, systems and methods according to present principles may provide valuable insight into mechanisms and factors influencing frailty status by quantifying the subject's PA, frailty related parameters, and user's vulnerability in all contexts, including everyday life.

In the field of drug development, systems and methods according to present principles may be employed to study the role of various drugs and treatment procedures on physical activity and frailty status of people during clinical studies.

In the fields of rehabilitation and physical therapy, systems and methods according to present principles provide valuable feedback on the user's improvement or enhancement in activity behavior and change in frailty and cognitive status.

In the fields of diet and weight management, systems and methods according to present principles provide intelligent feedback to the user about his or her daily energy expenditure and changes in muscle mass and strength.

In the fields of acute care and in hospital applications, frailty evaluation using systems and methods according to present principles provide valuable information to personalize the type of surgical or non-surgical intervention as well as in selection of appropriate diet, medication, and required care attention. In addition, it provides valuable information to nurses to optimize the intensity and amount of resource allocation to provide care to an inpatient population.

While specific examples of benefits and advantages are provided above, other benefits and advantages may also inure to various implementations of the invention, and not all benefits and advantages need be met in any particular implementation.

Specific indicators of frailty are now described.

Frailty Status

Aging is associated with progressive homeostatic dysregulation of the complex human system, resulting both from decreased function in multiple physiological systems, as well as loss of layers of feed forward and feedback mechanisms among interacting systems. Frailty results when these interconnected physiological systems cross a threshold of aggregate diminution in functioning. This diminution can result from aging-related physiological changes, and may be exacerbated by disease. Aggregated physiological dysfunction, and compromise of stress response mechanisms, underlie the frailty phenotype. The frailty phenotype has been operationalized and validated as the presence of three or more of the five following factors: low strength, low energy, slowed motor performance, low physical activity, or unintentional weight loss. Pre-frailty is associated with one or two of the above factors, and non-frailty with zero factors. Without wishing to be bound by theory, it is thought that this clinical syndrome is a result of dysregulated energetics linked to an increasingly homeostenotic physiology, including a proinflammatory state, anemia, abnormal hormonal levels, micronutrient deficiencies, sarcopenia, and possibly, decrements in neuromuscular control. Frail elders are at increased risk of poor clinical outcomes, including increased healthcare utilization, loss of independence, institutionalization and mortality, as well as the associated increased costs. Though frailty is known to be potentially remediable with physical therapy (PT), it remains unknown where in the frailty trajectory, or which specific rehabilitative components, are most remediable to intervention. Identification of early markers of frailty would allow early intervention and rehabilitation, prior to progression to a frail state beyond remediation.

Furthermore, gross clinical measures such as the "Timed Get Up and Go" test do not constitute precise early indicators of frailty. Examples of such early indicators include patterns of total daily activity or specific postural decrements. Interventions to date have focused on physical therapy; however, the relationship between individual decrements and specific PT interventions remains unknown because frailty measures are insensitive to the targeted intervention. Clinimetrically sound objective frailty measures are required to better identify and measure frailty and frailty outcomes. More precise early indicators of pre-frailty, and more specific measures of frailty components, are of key importance to enable targeted remediation. Remote methods are also desirable to track/identify elders at risk in the home environment while performing activities of daily living (ADLs).

Outcome measures that capture the dynamic nature of frailty, using a continuous or ordinal scoring system, may be of higher utility in tracking change in frailty status over time, as the same may provide more quantifiable results and thus enable and promote classification and stratification.

Remote activity monitoring according to present principles provides one particularly well-suited method to achieve this goal, as the same allows sensitive and specific characterization of patterns of total daily activity and specific postural decrements during ADL. This information may be employed for targeted intervention and outcome measurement, as well as for in-home remote monitoring to indicate decrements in overall activity and risk of frailty, as well as to provide effective intervention.

The systems and methods according to present principles may in one implementation employ accelerometer data to identify the type of postural transfer and which therefore enables long-term, autonomous, and real-time operation of the system. In some implementations such employment may be performed without the need of filtering.

in another implementation, systems and methods according to present principles allows accurate characterization of frailty related symptoms including one or more of slowness, weakness, flopping, exhaustion, and cognitive decline during activities of daily living. Without wishing to be bound by theory, these parameters may be valuable to allow better characterization of frailty, which in turn can provide clinical feedback to help identify the pathway of development of frailty and to personalize the type of intervention required to, in some cases, began or allow or promote the reversal of frailty.

In addition, in yet another implementation, the systems and methods according to present principles characterize the response of heart rate to a dynamic activity, as well as recovery of heart rate in response to a static activity subsequent to a dynamic activity. This information can be employed to identify frailty status without using sophisticated algorithms, and thus can be implemented in a low-cost and low-power processor to identify frailty status during activities of daily living in a convenient fashion.

In one aspect, the invention is directed towards a system to identify the presence and degree of frailty comprising: a wearable sensor module, configured to be attached to a person, the sensor comprising an accelerometer component configured to generate signals in response to motion or movements of the body, the signals comprising at least a frontal acceleration signal; and one or more processor circuits programmed to: identify a sit to stand or stand to sit postural transfer based on identifying a dynamic pattern before or after a peak detected in the frontal acceleration pattern; and derive information related to frailty status including non-frail, pre-frail, and frail, by identifying flopping, slowness, weakness, or exhaustion.

Implementations of this system may include one or more of the following. The sensor module may further include an accelerometer component configured to measure vertical accelerations, and the one or more processor circuits may be further programmed to identify a dynamic and a static activity based on standard deviation of the vertical or frontal accelerations in a pre-defined interval pre or post of a postural transfer. The one or more processor circuits may be further programmed to identify a standing posture if a dynamic activity and a static activity are identified immediately after and before a postural transfer, respectively. The one or more processor circuits may be further programmed to identify a sitting posture if a static activity and a dynamic activity are identified immediately after and before a postural transfer, respectively. The one or more processor circuits may be further programmed to measure a speed of low intensity movement based on integration of acceleration during a static activity and then removing the slope of integration during a pre-defined interval.

The one or more processor circuits may be further programmed to measure a speed of a high intensity movement based on integration of acceleration during a dynamic activity and then removing the drift of integration using a high pass filter during a pre-defined interval. The one or more processor circuits may be further programmed to identify frailty status by measuring a number of flopping events occurring within a pre-defined interval by identifying the number of immediate transfers from a dynamic activity to a static activity with a transfer speed of greater than a pre-defined threshold. The one or more processor circuits may be further programmed to identify frailty status by measuring slowness of movement as characterized by measuring the duration, or magnitude of acceleration, or magnitude of velocity, for completing a postural transfer or a dynamic activity. The one or more processor circuits are further programmed to identify frailty status by measuring weakness as characterized by measuring the standard deviation of frontal or vertical accelerations or magnitude of speed during a dynamic activity. The one or more processor circuits may be further programmed to identify cautious-sitting by detecting a sequence of a dynamic activity followed by a static activity followed by stand to sit postural transfer. The one or more processor circuits may be further programmed to identify frailty status by measuring a number of cautious-sitting events occurring within a pre-defined interval.

The one or more processor circuits may be further programmed to identify frailty status by measuring exhaustion as characterized by measuring the slope and change in speed or acceleration of movement during cyclic activities such as walking, consecutive sit to stand postural transfers, or consecutive body joint flexion and extension. The one or more processor circuits may be further programmed to identify frailty status based on measuring a cognitive problem as characterized by measuring non-uniformity of step-to-step walking speed by measuring fluctuations in the walking speed. The one or more processor circuits may be further programmed to measure body sway based on measuring acceleration and speed during standing posture. The one or more processor circuits may be further programmed to identify frailty status by characterization of body sway during open-loop and closed-loop conditions. The one or more processor circuits may be further programmed to identify open-loop and closed-loop conditions by measuring a body sway fluctuation curve as estimated by the time series average of square value of body sway during a series of progressive time intervals during standing, wherein the open-loop and closed-loop conditions are separated by identifying best linear fits on the body sway fluctuation curve.

The one or more processor circuits may be further programmed to identify frailty status by linear or non-linear combination of two or more parameters measured as described above.

The wearable sensor module may be configured to be attached to the upper body of a person. The sensor module may be further configured to measure a vertical acceleration signal.

In another aspect, the invention is directed towards a system to identify the presence and degree of frailty comprising: a wearable sensor module, configured to be attached to a person, the sensor comprising an accelerometer component configured to generate signals in response to motion or movements of the body, the signals comprising at least a frontal acceleration signal, and a sensor to measure heart rate or electrocardiogram (ECG) pattern; and one or more processor circuits programmed to: identify a sit to stand or stand to sit postural transfer based on identifying a dynamic pattern before or after a peak detected in the frontal acceleration pattern; and derive information related to frailty status including non-frail, pre-frail, and frail, by identifying flopping, cautious-sitting, slowness, weakness, or exhaustion. The one or more processor circuits may be further programmed to identify frailty based on identifying premature junctional contractions (PJC) episodes through electrocardiogram monitoring. The frailty status could be then identified by measuring the number and duration of PJC episodes during a pre-defined time interval.

Implementations of this system may include one or more of the following. The one or more processor circuits may be further programmed to identify, confirm and define frailty status based on measuring rate and magnitude of change in heart rate from a static activity to a dynamic activity occurring in a predefined interval and with a pre-defined duration. The one or more processor circuits may be further programmed to identify frailty status based on measuring rate and magnitude of changes in heart rate from a dynamic activity to a static activity occurring in a predefined interval and with a pre-defined duration.

In yet another aspect, the invention is directed towards a system to identify the presence and degree of frailty comprising: a wearable sensor module, configured to be attached to a person, the sensor comprising an accelerometer component configured to generate signals in response to motion or movements of the body, the signals comprising at least a frontal acceleration signal, and a sensor to measure respiration rate; and one or more processor circuits programmed to: identify a sit to stand or stand to sit postural transfer based on identifying a dynamic pattern before or after a peak detected in the frontal acceleration pattern; and derive information related to frailty status including non-frail, pre-frail, and frail, by identifying flopping, cautious-sitting, slowness, weakness, or exhaustion.

Implementations of this system may include one or more of the following. The one or more processor circuits may be further programmed to identify frailty status based on measuring rate and magnitude of change in respiration rate from a static activity to a dynamic activity occurring in a pre-defined interval and with a pre-defined duration. The one or more processor circuits may be further programmed to identify frailty status based on measuring rate and magnitude of change in respiration rate from a dynamic activity to a static activity occurring in a predefined interval and with a pre-defined duration.

In yet another aspect, the invention is directed towards a system to identify the presence and degree of frailty comprising: a wearable sensor module, configured to be attached to a person, the sensor comprising an accelerometer component configured to generate signals in response to motion or movements of the body, the signals comprising at least a frontal acceleration signal, and a sensor to measure audio; and one or more processor circuits programmed to: identify a sit to stand or stand to sit postural transfer based on identifying a dynamic pattern before or after a peak detected in the frontal acceleration pattern; and derive information related to frailty status including non-frail, pre-frail, and frail, by identifying flopping, cautious-sitting, slowness, weakness, or exhaustion.

Implementations of this system may include one or more of the following. The one or more processor circuits may be further programmed to identify whether the user is talking based on measuring a magnitude of audio and a change in upper body acceleration or respiration rate. The one or more processor circuits may be further programmed to: measure a gait difference including a change in speed, or cadence, or step-to-step duration variation between the conditions where the user is talking and when the user is not talking. The one or more processor circuits may be further programmed to identify frailty status if the walking difference between conditions with and without talking exceeds a pre-defined threshold.

Other advantages and features of the invention will be apparent from the description that follows, including the drawings and claims.

This Summary is provided to introduce a selection of concepts in a simplified form. The concepts are further described in the Detailed Description section. Elements or steps other than those described in this Summary are possible, and no element or step is necessarily required. This Summary is not intended to identify key features or essential features of the claimed subject matter, nor is it intended for use as an aid in determining the scope of the claimed subject matter. The claimed subject matter is not limited to implementations that solve any or all disadvantages noted in any part of this disclosure.

BRIEF DESCRIPTION OF THE DRAWINGS

The foregoing and other objects, features, and advantages of the invention will be apparent from the following detailed description of invention, as illustrated in the accompanying drawings, in which like reference numerals designate like elements throughout. Elements are not to scale unless otherwise noted.

DETAILED DESCRIPTION

Figure 1:
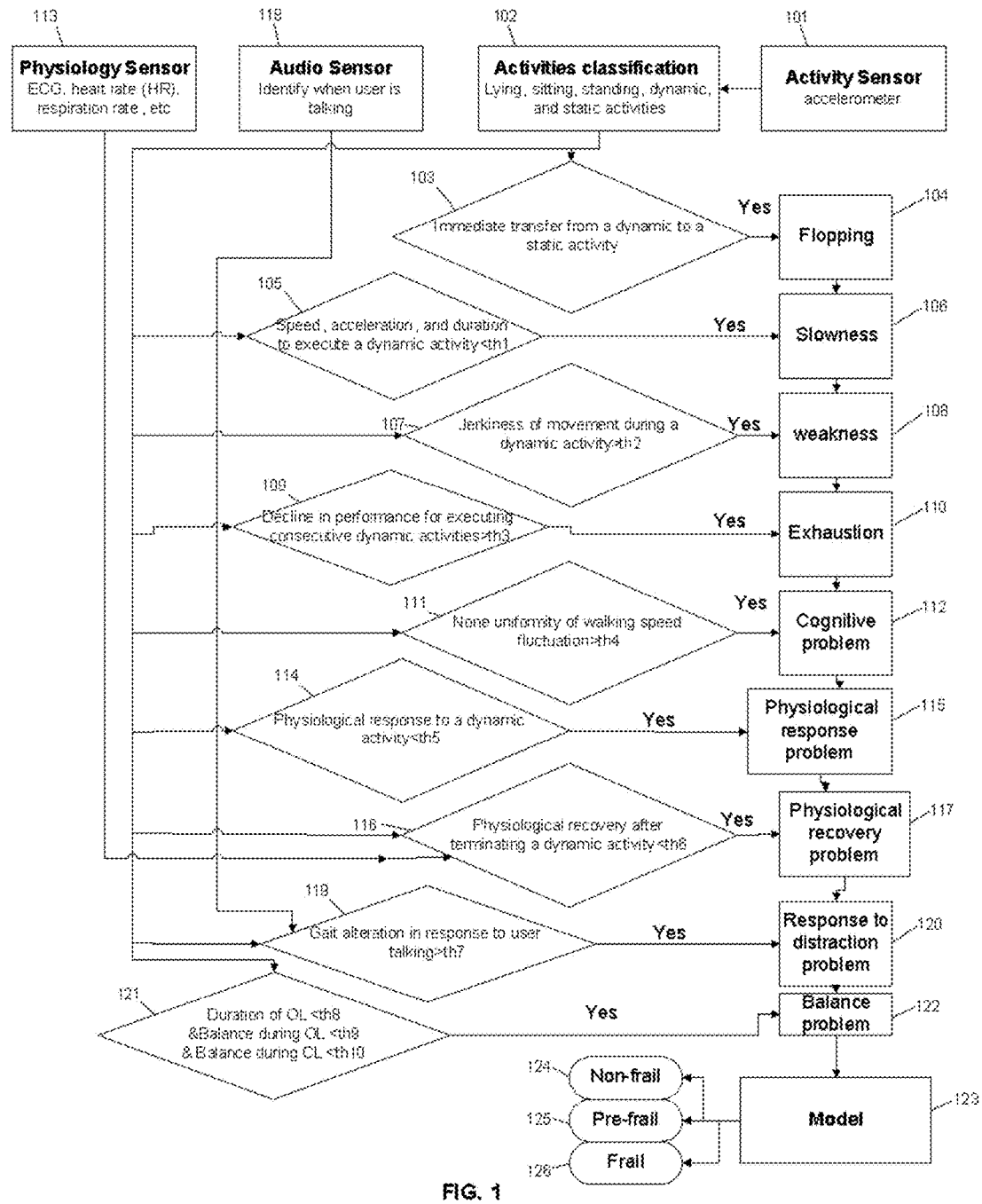
FIG. 1 illustrates exemplary methods used to determine frailty status based on scoring one of more elements related to user's flopping frequency, slowness, weakness, exhaustion, cognition, physiological response to activities, physiological recovery from activities, response to distraction, and balance problems.

The following descriptions and examples illustrate some exemplary embodiments of systems and methods according to present principles in detail. Those of skill in the art will recognize that there are numerous variations and modifications of the systems and methods that are encompassed by its scope. Accordingly, the description of certain exemplary embodiments should not be deemed to limit the scope of the present invention.

Systems and methods according to present principles provide ways for performing one or more of the following tasks during a subject user's everyday life: 1) monitoring the user's physical activity; 2) assessing and identifying frailty-related activity biomarkers including slowness, weakness, flopping, cautious-sitting, exhaustion, and cognitive decline during activities of daily living; 3) evaluating one or more physiological responses including heart rate, heart rate variability, respiration rate, and skin temperature to dynamic and static activities; and 4) identifying frailty status using one or more activity biomarkers and physiological responses to activities. The second, third, and fourth tasks may be based on the results obtained from the first.

The system includes a sensing module (SM), which may be attached to the user's body for measuring body movements. In one implementation, the sensing module includes one to three axial accelerometers. In one exemplary configuration, at least one accelerometer is configured to measure acceleration in the frontal direction, which is defined to be the direction perpendicular to the frontal plane of the user.

The SM may also include optional physiological and audio sensors, which are configured to measure physiological data (e.g. heart rate, respiration rate, skin temperature) and/or audio signals.

Sensors may include any sensing elements which allow the measurement of body motions including in particular acceleration, velocity, position, or orientation. Such may include sensors based on Micro-Electro-Mechanical Systems (MEMS) technology (e.g. piezo-resistive, or electro-magnetic sensors) or optical sensors (e.g. camera based systems, laser sensors, etc), or any other type of motion tracking sensors. SM may include those measuring from single to multiple degrees of freedom, including x, y, z, pitch, roll, yaw or any combination thereof. The sensors may be wearable, such as on eyeglasses, apparel, watches, or the like.

The SM may also include a data-storage system for storing the measured data. An optional on-board communications system provides the SM the capability to transmit the collected data and/or analyzed signals through either wired or wireless links for storage and/or further offline analysis. Data storage may include any type of memory such as static or dynamic random-access memory, or non-volatile memory. Other types of data storage will also be understood, including data storage on a means on the user, e.g., flash storage, for later transmission or downloading to a computing device.

In one implementation, the system can display frailty status using an embedded multiple color LED or digital screen indicating frailty status. Other types of displays will also be understood. In addition, the system may remotely display relevant information such as frailty status, e.g., non-frail, pre-frail, frail, or a score of frailty status, history of frailty status, as well as status and history of each measured parameter, e.g., physical activities, flopping, slowness, weakness, cognition, exhaustion, cognitive problem, physiological response problem, physiological recover problem, response to distraction problem, and balance problem. Each of the measured parameters may be displayed either in a binary fashion, e.g., 0=healthy, 1=problem or unhealthy, or mapped to a scoring system, e.g., on a scale from 0 to 5, where a higher number indicates more deviation from a healthy status. The data can be transferred via Bluetooth, WiFi, other radio frequency protocols, and any other means of data communication.

Analysis of the measured signals may be carried out entirely on board the SM, partially on board the SM and partially at other location(s), or entirely at other location(s). If the analysis is carried out, whether partially or fully, on board the SM, the SM also includes a microprocessor that fully or partially performs the described methods. Certain alternative embodiments can utilize a computer system other than a microprocessor to perform the methods described herein. For example, an application-specific integrated circuit (ASIC) can be used to perform some or all of the described methods.

In another configuration the system may include a group, collection assembly, or ensemble of sensors that may be placed on multiple locations on the body. These sensors may function individually, collectively, or with cross-talk. An array of sensors may be located on multiple locations on the body. Sensors may also be located within the body—either in orifices, e.g., mouth, ear, urethra, vagina, anus or in the body corpus, e.g. as subcutaneous, intradermal, intramuscular, or via percutaneous or surgical placement.

Monitoring the User's Physical Activity

Monitoring the user's physical activity may include monitoring and assessing the user's postures, dynamic activities, static activities, as well as frailty-related parameters. To this end, systems and methods according to current principles may compute various parameters associated with the user's frailty and cognitive status from the data recorded by the SM as illustrated in the flowchart of FIG. 1. The assessed parameters may include flopping (step 104), slowness (step 106), weakness (step 108), exhaustion (step 110), cognitive problems (steps 112 and 120), and physiological problems (steps 115 and 117).

FIG. 1 also illustrates various other sensors, which may be employed, as well as other aspects. For example, physiology sensors 113 may be employed to measure an electrocardiogram (ECG), heart rate, respiration rate, temperature, blood pressure, or the like, and the same may feed into physiologic data, especially pertaining to physiological recovery determinations in step 116. Audio sensors 118 may be employed to identify when a user is speaking, and such may be employed when testing in step 119 if gait is altered when the user is speaking Activity sensors such as accelerometers 101 may be employed to determine user activity in an activities classification step 102. An accelerometer, or alternatively another sensor, such as a GPS or the like, may be employed to determine if the user is lying down, sitting, standing, performing dynamic activities, or performing static activities. Such activities classification may feed into step 103 of determining flopping, step 105 of determining speed or slowness, step 107 of determining weakness or jerkiness of movement, step 109 of determining decline in performance due to exhaustion, step 111 of determining non-uniformity of walking speed, indicating a potential cognitive problem, step 114 of determining physiological responses to dynamic activity, and step 119 of determining gait alteration in response to speaking. In one or more of these cases it will be understood that such measurements may be compared to threshold values th1 to th10 in the determination of frailty, as indicated in the figure.

Use of accelerometers in place of gyroscopes, and using the characterization of dynamic and static activities pre and post a postural transfer by systems and methods according to present principles, allows for long-term autonomous operability and low cost of the system. The associated challenges introduced by this replacement, however, include extracting meaningful data associated with frailty and cognitive decline from commonly-noisy accelerometer signals during everyday living activities. In addition, using supplementary sensors for measuring physiological response and recovery to and from a dynamic activity, as well as using audio sensors to measure activity performance deterioration due to talking, may enhance the accuracy of frailty classification during activities of daily living.

The method corresponding to the flowchart of FIG. 1 may be employed to indicate how information from various sensors can lead to the determination of the problems noted, e.g., flopping, slowness, etc. In most cases a signal from an activity sensor 101 is employed, and in certain cases a sensor for measuring a physiological parameter 113 is also used. An audio sensor 118 may also be used in special circumstances, in particular for the identification of gait alterations when the user is talking. The activity sensor 101 may be employed and used in a step of activities classification 102, which may in turn be employed to detect various activity-based movements, and to determine variables appropriate for frailty measurement and evaluation. Particular variables are described in greater detail below, but it will be noted that the determination of the various variables flows into a model 123 from which the determination and evaluation of a subject user's frailty is categorized, classified, or stratified, e.g., into a non-frail condition 124, a pre-frail condition 125, or a frail condition 126.

Figure 2:
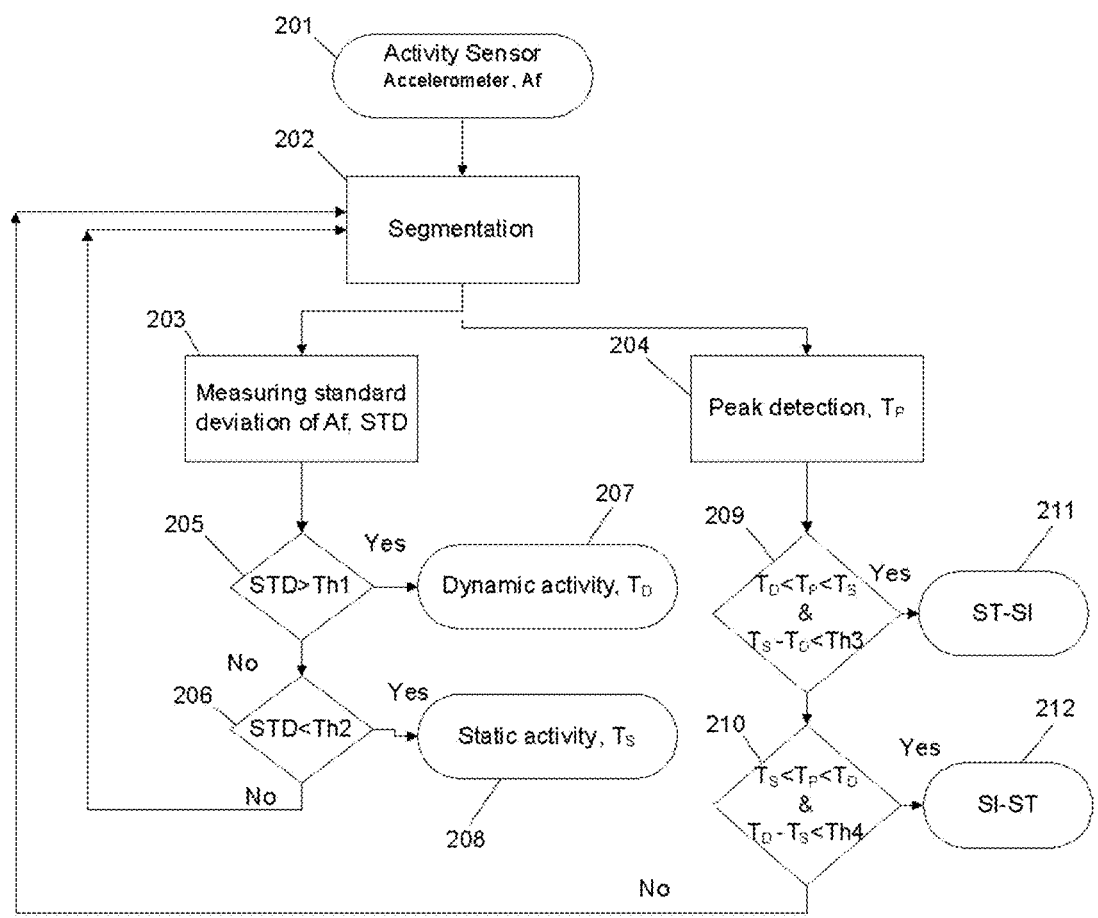
FIG. 2 illustrates methods used to classify activities including dynamic and static activities as well as postural transition from sit to stand or stand to sit.

The flowchart of FIG. 2 demonstrates how dynamic activity, static activity, and postural transfers (in this case, SI-ST and ST-SI) are detected during everyday moments. The algorithms use a signal from a frontal accelerometer 201, e.g., the frontal accelerometer signal (Af). As shown in FIG. 2, the algorithm performs the following steps on the frontal accelerometer signal to determine occurrence and type of postural transitions, as well as dynamic and static activities, which are believed to be of key importance in the evaluation of frailty status.

In step 202, acceleration data as measured by the activity sensor 201 undergoes a process of segmentation.

Then, in steps 203, 205, 206, 207, and 208, the standard deviation of the frontal accelerometer signal (STD) is computed and used to identify the time of occurrence and duration of dynamic ($T_D$) or static ($T_S$) activity bouts. In particular, and in one implementation, if the standard deviation varies by greater than a predetermined amount, the activity is determined to be a dynamic activity. In this implementation, if the standard deviation is less than a predetermined threshold, then the activity is determined to be a static activity.

The peak in the frontal accelerometer reading is then detected to identify the time of postural transfer ($T_p$) in step 204.

The sequence of dynamic and static activities pre and post a postural transfer within a pre-defined time interval is then evaluated in steps 209, 210, 211, and 212. For example, if the sequence is dynamic activity, then postural transfer, then static activity, and the time differential between the dynamic activity and the static activity is less than a predetermined amount, then the postural transfer is characterized as standing-to-sitting (ST-SI). As another example, if the sequence is static activity, then postural transfer, then dynamic activity, and the time differential between the static activity and the dynamic activity is less than a predetermined amount, then the postural transfer is characterized as sitting-to-standing (SI-ST).

Specific frailty indications shown in FIG. 1 are now described in greater detail.

Identification of Flopping

Figure 3:
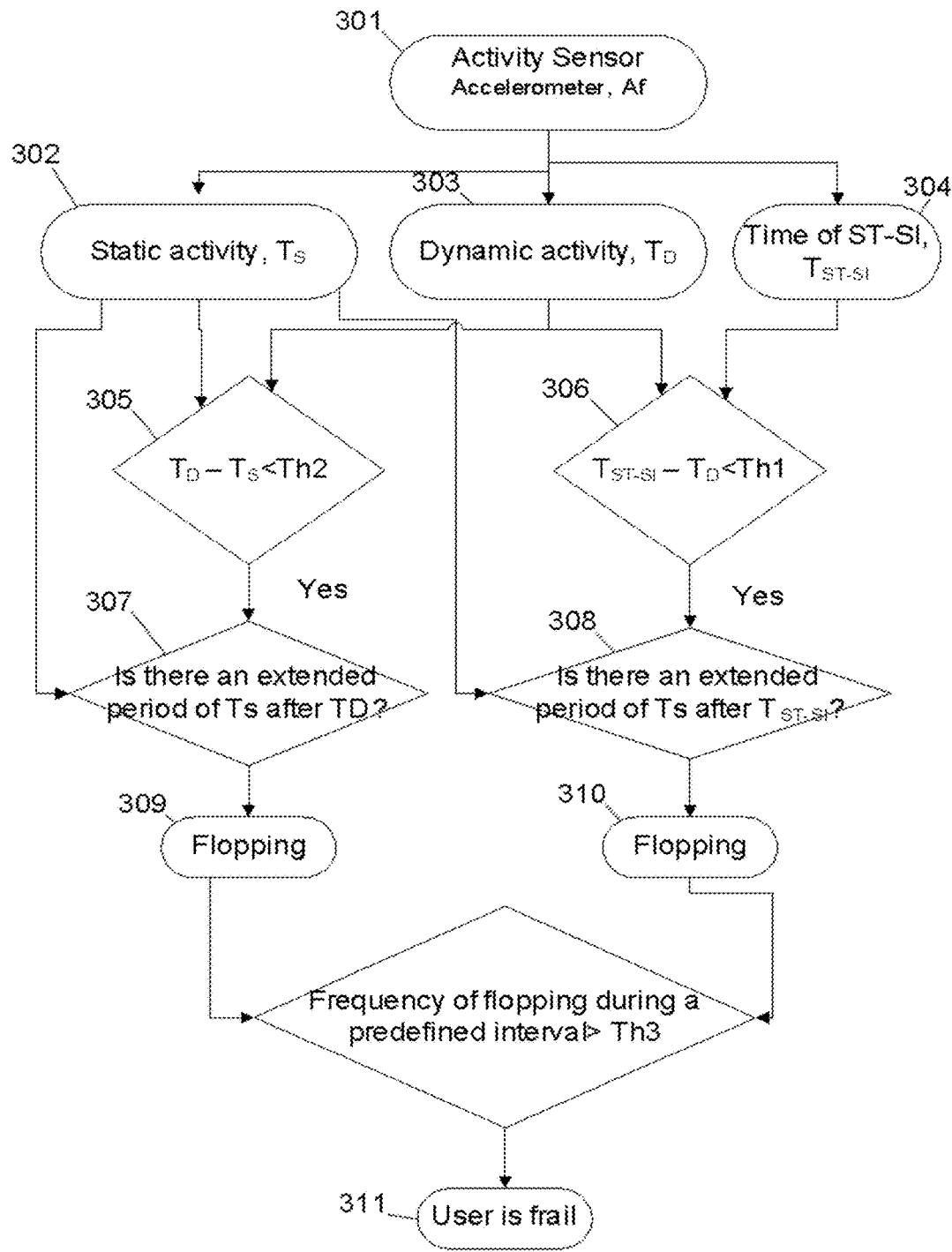
FIG. 3 illustrates methods used to identify flopping.

Flopping (determined in step 104 in FIG. 1) is identified or defined as the occurrence of a sudden postural transfer between a dynamic activity to a prolonged static activity or an immediate transfer from a dynamic activity to a sitting or lying posture followed by a prolonged static activity. The flowchart of FIG. 3 illustrates different steps which may be employed in one exemplary method to identify flopping. First, in steps 302 and 303, bouts of static and/or dynamic activity are identified. In step 304, the time of occurrence of postural transfers to sitting or lying are identified through an activity sensor, or sensor module (step 301) as described previously. Flopping can then be identified via several approaches. Two exemplary approaches are described in the following: 1) if a prolonged static activity occurred immediately after a dynamic activity, as determined by steps 305 and 307; or 2) if a postural transfer occurred immediately after a dynamic activity followed by a prolonged static activity, as determined by steps 306 and 308. By analysis of steps 307 and 308, the amount of flopping may be identified in steps 309 and 310. A frail person is identified by the total numbers of flopping events occurring in a predefined period of time, and in particular if the total number in the predefined period of time is greater than a threshold, in which case the subject user is identified as frail in step 311. Any postural changes may be classified as flopping, e.g., sit to stand, walk to sit, sit to lying, and so on, and combinations of these may be measured in the same time period. Cautious-sitting could be identified by identifying a sequence of dynamic activity followed with a static activity with duration exceeding a pre-defined threshold followed by a stand to sit or stand to lying postural transfer.

Identification of Slowness:

Slowness is identified by time required to execute specific motor tasks such as sitting to standing, lying to sitting, initiation of walking, turning, elbow flexion and extension, etc. A frail person may be identified when execution of a specific motor task exceeds a predefined threshold defined for that specific task.

In more detail, slowness may be identified by the time, velocity, and acceleration required to execute a pre-defined dynamic activity. Some of the dynamic activities of interest include but are not limited to high energy activities as identified by dynamic activities with a measured standard deviation of greater than a pre-defined threshold, cyclic activities (e.g. walking, climbing or descending stairs, turning, etc) as identified by the occurrence of repetitive acceleration peaks during a dynamic activity, SI-ST, ST-SI, initiation of walking, etc. Specific motor tasks such as sit-to-stand, lying-to-sit, initiation of walking, turning, elbow flexion and extension, etc., may also be included. The velocity of a dynamic activity may be estimated by integration of acceleration in a pre-defined interval followed by application of a high pass filter, which may be used to remove the drift due to integration. If the standard deviation of acceleration during the interval of integration is lower than a threshold, e.g., for velocities during static or low-intensity activities, the drift of integration may be removed by subtracting a best fit line from the integrated signal instead of using a high pass filter. This technique is useful to prevent filtering the useful data related to the speed of movement. A frail person is identified when execution of a specific dynamic activity exceeds a pre-defined threshold or when the velocity and/or acceleration to execute a specific dynamic activity is below a pre-defined threshold.

Identification of Weakness:

Weakness is identified by measuring jerkiness of movement during transfer from one posture to another, or when starting a walking or turning activity. The jerkiness of movement can be measured by the coefficient of variation (standard deviation/average value) of a kinematic parameter, e.g., speed. In addition, weakness may be identified by a limited range of motion of a specific joint, e.g., knee, or a specific body segment e.g., trunk. A frail person is generally identified by increased weakness.

In more detail, weakness during activities of daily living is identified when the jerkiness of movement while executing a pre-defined dynamic task exceeds a pre-defined threshold. The jerkiness of movement can be identified by measuring the standard deviation of acceleration signals in different directions and in a pre-defined interval. Some of the dynamic activities of interest to identify weakness include, but are not limited to, high energetic activities, cyclic activities, e.g. walking, climbing or descending stairs, turning, etc, SI-ST, ST-SI, initiation of walking, initiation of postural transfer, etc. A frail person is identified when the number of identified weakness events exceeds a pre-defined threshold.

Identification of Exhaustion:

Exhaustion is identified by a lack of consecutive activities during a predefined time interval, such as a low number of consecutive steps, few postural transfers, limited trunk bending, few elbow flexions or extensions, or the like.

Exhaustion is identified by measuring changes in the quality of performance of pre-defined dynamic activities that are repeated consecutively. Quality of performance may be identified by measuring speed, acceleration, and timing, for the execution of a pre-defined dynamic task. Some of the dynamic activities of interest to identify exhaustion include, but are not limited to, cyclic activities, e.g., walking, climbing or descending stairs, turning, etc., consecutive SI-ST or ST-SI postural transfer, body segment flexion and extension, etc. Quality of performance may be quantified further by measuring the rate of reduction in speed and acceleration for performing consecutive dynamic activities, e.g. walking, turning, consecutive body segment flexion and extension, etc. A frail person is identified when the number of identified exhaustion events exceeds a pre-defined threshold.

Identification of Cognitive Problem:

Cognitive problems during activities of daily living may be identified using several approaches. Two exemplary ones are described below.

Figure 4:
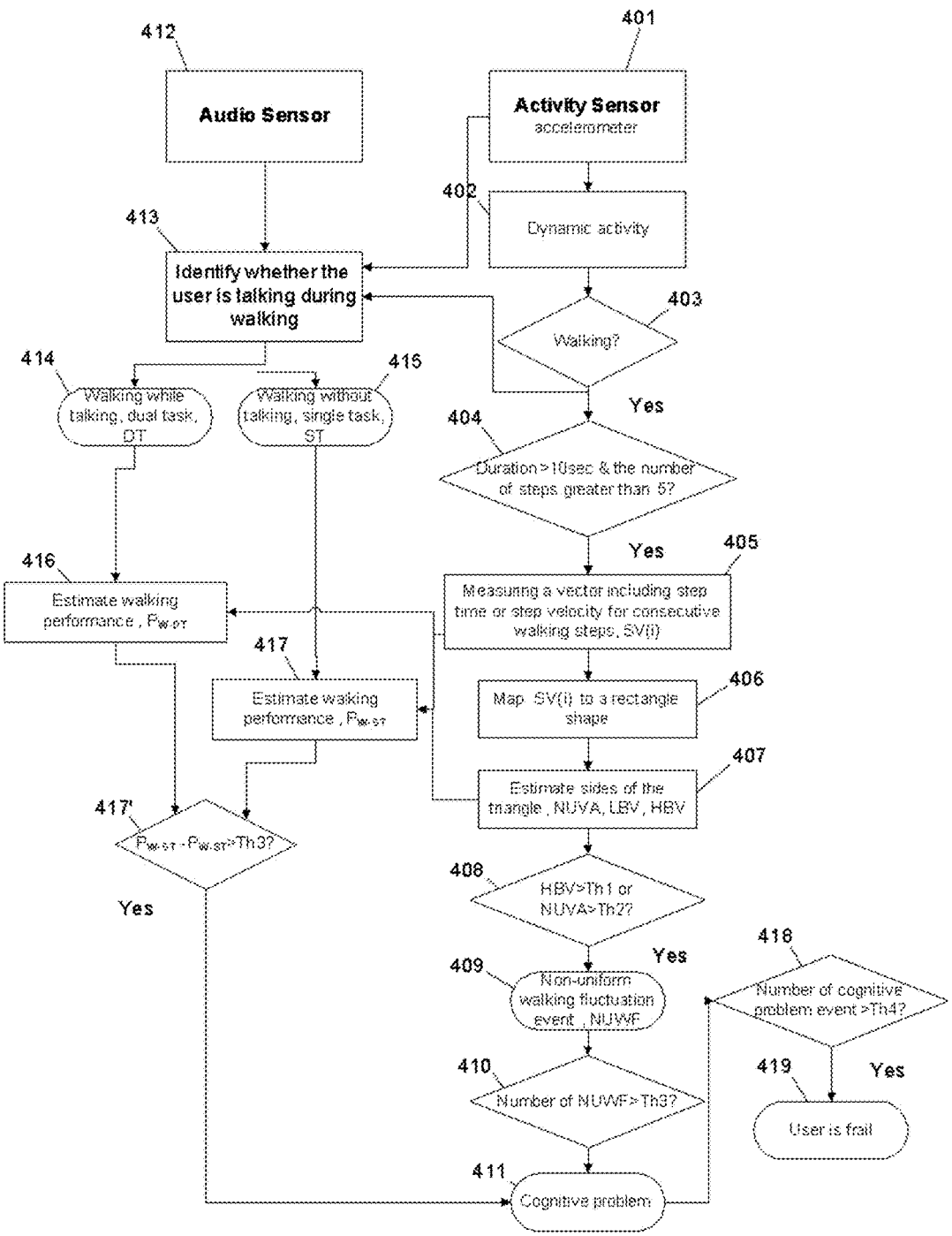
FIG. 4 illustrates methods used to identify cognitive problems via assessing non-uniformity in gait fluctuations or changes in performance of walking in response to talking.

Method 1: In a first method, cognitive impairment is assessed by identification of non-uniformity of walking speed fluctuation (step 111 in FIG. 1). The act of walking itself is recognized when at least three consecutive acceleration peaks are identified within a pre-defined interval during a dynamic activity. Referring to FIG. 4, the recognition of walking is performed by an activity sensor 401 such as an accelerometer which by sensing movement determines in step 402 that dynamic activity is occurring. In step 403, whether the dynamic activity is walking is determined. The identified acceleration peaks, which satisfy a time difference between two consecutive peaks, are considered as walking steps. Fluctuation assessment is performed when at least 10 seconds of a walking and five steps of walking are recognized during activities of daily living, which is determined in step 404.

Non-uniform walking fluctuations are defined based on uneven gait acceleration and deceleration compared to a mean value. In more detail, the fluctuations are estimated based on mapping a step-to-step gait fluctuation to a right triangle shape where the location of its vertices are estimated using minimum, maximum, and mean, of gait parameters. The hypotenuse value may be assumed to represent the non-uniformity of gait fluctuation (NUVA) and the two other sides represent lower band (LDV) and higher band (HBV) of gait variability. A frail person is identified by high non-uniformity of gait fluctuation and long HPV.

Figure 5:
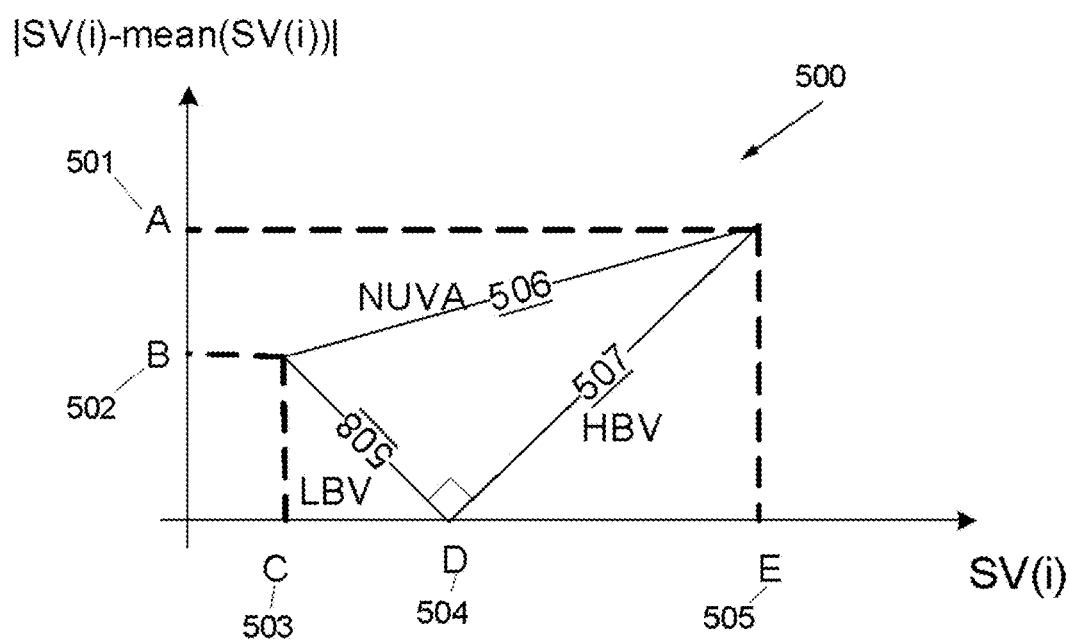
FIG. 5 is an illustration of an exemplary definition of non-uniformity in gait fluctuation.

Specifically, non-uniformity in walking, e.g., fluctuations, are assessed by measuring, in step 405, and mapping, in step 406, the vector of consecutive step velocity or step time for each walking step (SV(i)) to a triangle as illustrated by the graph 500 of FIG. 5. The y-values A (501 in FIG. 5) and B (502 in FIG. 5) are estimated using the following formulas:

Point A: |max(SV(i))−mean(SV(i))|
Point B: |min(SV(i))−mean(SV(i))|

Where, 'max' and 'min' represent maximum and minimum values of vector of SV(i).

The x-values C (503 in FIG. 5), D (504 in FIG. 5), and E (505 in FIG. 5) are estimated using the following formulas:

Point C: Min (SV(i))
Point D: Mean (SV(i))
Point E: Max(SV(i))

As noted, the hypotenuse length (506 in FIG. 5) represents the non-uniformity of gait fluctuation (NUVA) and the two sides of the hypotenuse represent a lower band (LBV, 508 in FIG. 5) and a higher band (HBV, 510 in FIG. 5) of gait variability. In other words, the hypotenuse, representing a measure of the variation in the subject user's gait, provides a sensitive measure for variation. This approach for estimating gait variability is generally more sensitive to cognitive deficits than measuring a standard deviation or coefficient of variation of gait variability. Consequently, in this method, the sides of the triangle are estimated (NUVA, LBV, and HBV) in step 407.

Figure 6:
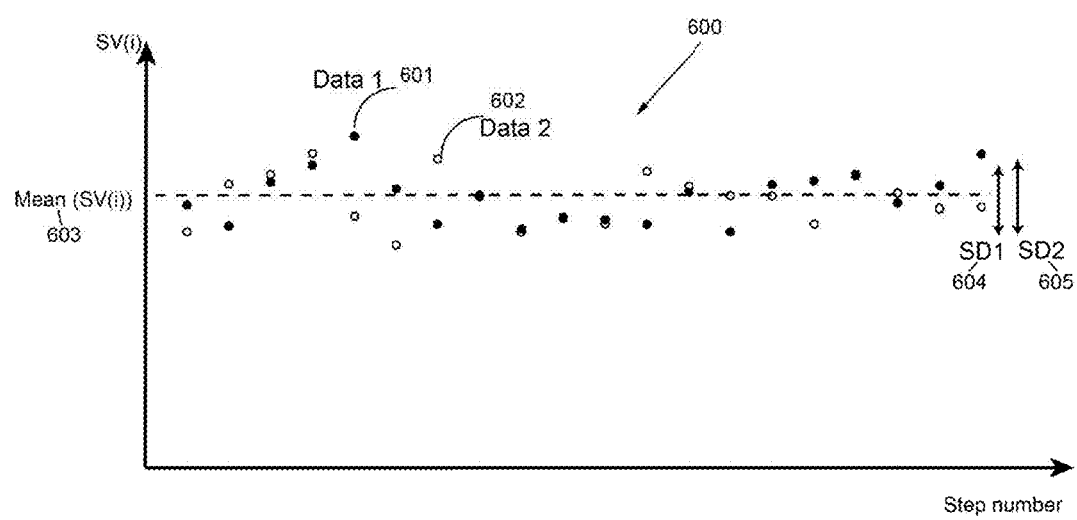
FIG. 6 is an illustration of gait speed fluctuation for a typical frail subject (Data 1, filled circle points) and a typical non-frail subject (Data 2, empty circle points). Using traditional gait variability assessment, e.g., the standard deviation of gait speed fluctuation, the two cases are difficult to distinguish.
Figure 7:
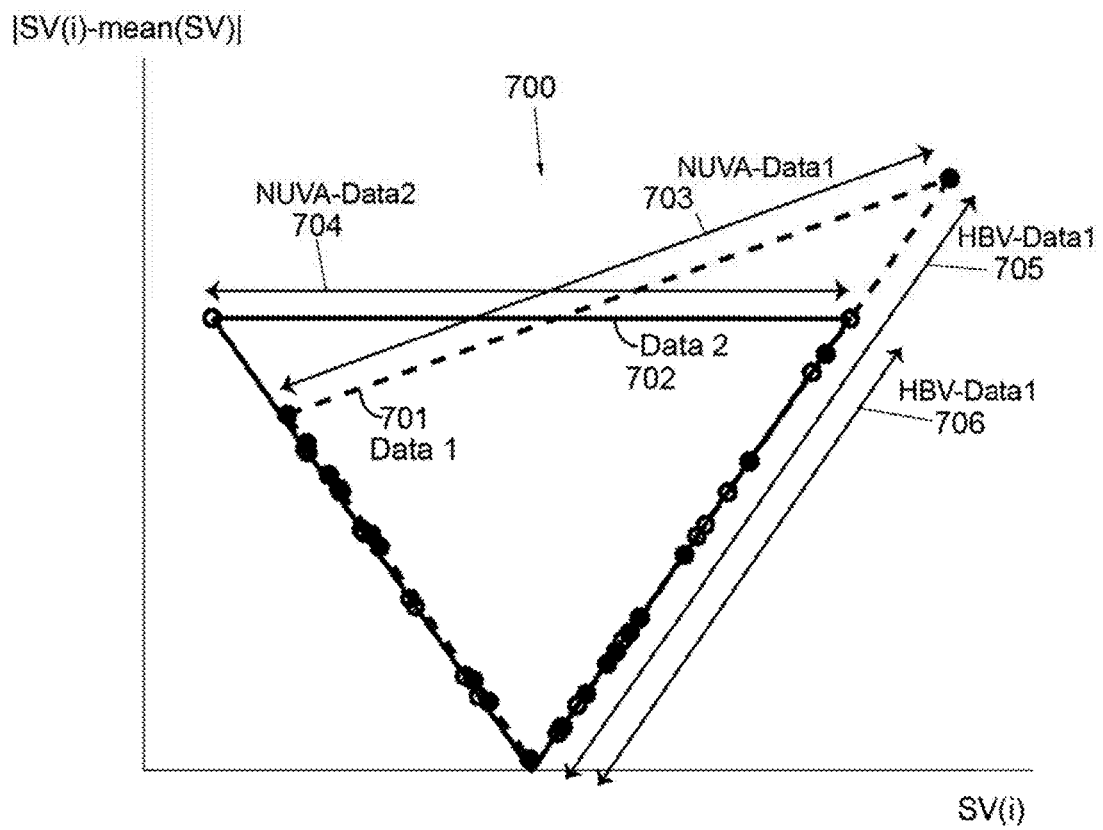
FIG. 7 is an illustration of non-uniformity in gait fluctuation for a typical frail case (Data 1, dashed line trace) and a typical non-frail case (Data 2, solid line trace). Using a non-uniformity approach, the two cases can be separated.

FIG. 6 illustrates two typical cases, one subject with a cognitive problem (Data 1, indicated by 601 and represented by closed circles) and one without a cognitive problem (Data 2, indicated by 602 and represented by open circles). Both subjects have the same mean value of step velocity, indicated by 603, and almost the same standard deviation of step velocity, indicated by 604 and 605. Thus measuring standard deviation or coefficient of variation as defined by standard deviation divided by mean value multiplied by 100 is not sensitive enough to evaluate cognitive deficit and thus cannot be used. However, as illustrated in FIG. 7, after mapping to a triangle shape as described above, NUVA, indicated by 703 and 704, and HBV values, indicated by 705 and 706, allow discriminating between two subjects, one with a cognitive deficit, indicated by 701, and another subject without a cognitive deficit, indicated by 702.

Referring back to FIG. 4, in steps 408 and 409, walking is classified as a high non-uniform walking fluctuation (NUWF) when either or both of NUVA and HBV exceed a pre-defined threshold. In steps 410 and 411, a subject is identified as having a cognitive problem if the number of NUWF exceeds a pre-defined threshold.

Method 2: For identifying a user's cognitive problem using another exemplary method, an optional sensor 412, configured to measure an audio signal, is required. In this method, during walking, the audio sensor is used to evaluate whether the subject is talking (i.e., dual task) or not (i.e., single task) in step 413. To ensure that the source of the audio signal is the subject, the information from a chest acceleration signal may also be evaluated to confirm that the identified sound is coming from the user. Then, in steps 414 and 415, the performance of walking during identified single task walking bout(s) and dual task walking bout(s) are recorded during a pre-defined interval (e.g., 24 hours) and compared. If the walking performance during dual tasks is lower than a pre-defined threshold, which may be based on the individual's single task walking performance, as determined in steps 416, 417, and 417', then the user is classified as a subject with a cognitive problem. Walking performance can be characterized using gait variability by the method described above, or using a traditional method based on standard deviation of walking speed fluctuation, step time, step velocity, etc.

Based on the number of walking bouts identified as having high gait speed fluctuations, as determined by method 1 above, or the magnitude of gait performance deterioration during dual task conditions, as determined by method 2 above, the frailty status of the user can be identified (steps 111 and 120 in FIG. 1). In FIG. 4, if a cognitive problem is identified at step 411, and if the number of cognitive problem events is greater than a threshold or greater than a threshold over a predetermined duration of time, as calculated by step 418, then the user may be determined to be frail in step 419.

Wandering is another variable related to frailty. Wandering can be characterized by short walking bouts among standing bouts. A frail person may be identified by the ratio of the total number of walking bouts to the total number of standing bouts, recorded in a predefined time interval.

Identification of Physiological Problems:

Frailty may also be identified by other physiological responses including abnormal physiological responses to activities such as a sudden increase in respiration rate, changes in skin temperature, or the like, in response to specific physical activities, e.g., rising from a chair, turning, sitting on a bed, or the like.

Physiological biomarkers associated with frailty may also be monitored during activities of daily living by adding one or more optional sensors which are able to monitor heart rate and/or other parameters. A similar approach can be also implemented by adding sensors able to measure respiration rate, skin temperature, etc. Alternatively, heart rate could be directly measured by an accelerometer attached on a pre-defined location such as noise, wrist, ear, etc., and configured to to capture heart beat via measurement of an acceleration pattern.

Figure 8:
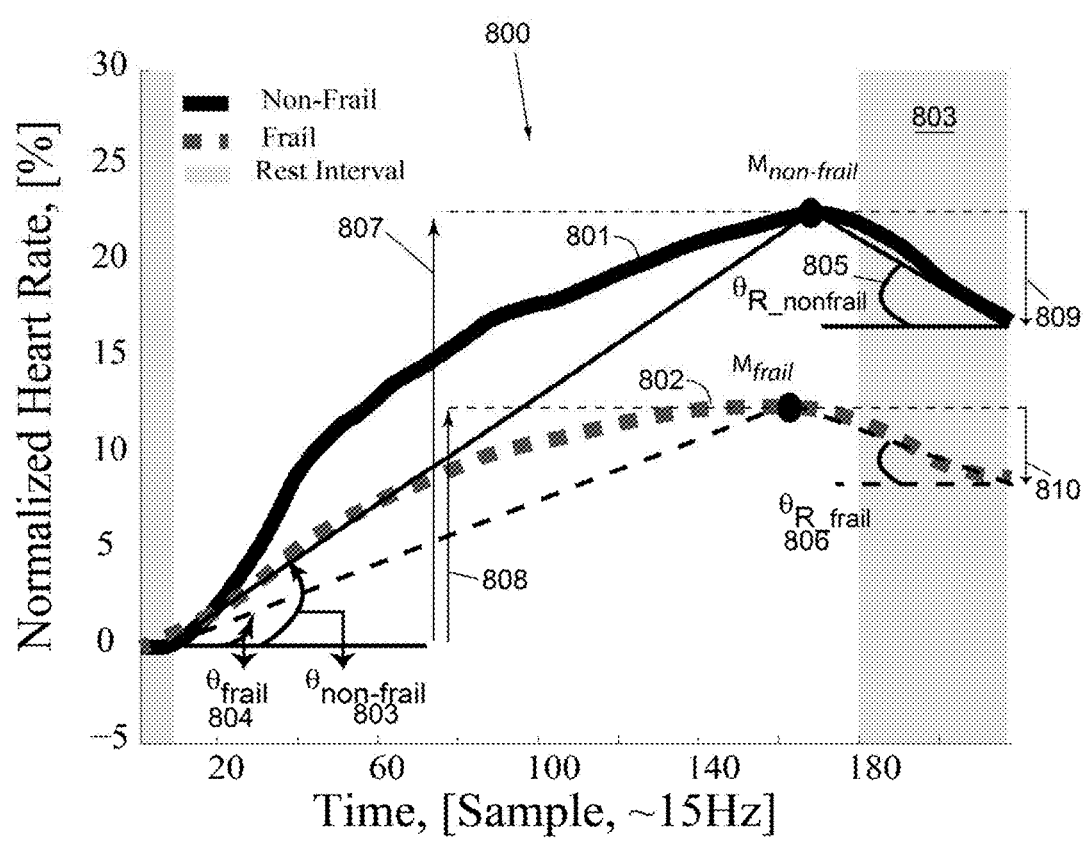
FIG. 8 is an illustration of heart rate response to, and heart rate recovery from, a dynamic activity for a frail case (dashed line trace) and for a non-frail case (solid line trace).

For example, FIG. 8 illustrates a typical heart rate response of a frail subject in trace 802 and that of a non-frail subject in trace 801. The dynamic activities of interest are (but are not limited to): SI-ST, ST-SI, cyclic activities, e.g. walking, turning, climbing stairs, high energetic dynamic activities, etc. Heart rate response is characterized by assessing the slope of heart rate increase in response to a high energetic activity, e.g., sit to stand, and/or recovery after executing a high energetic activity. Accordingly, a frail person is generally identified by a slow response and a slow recovery.

Figure 9:
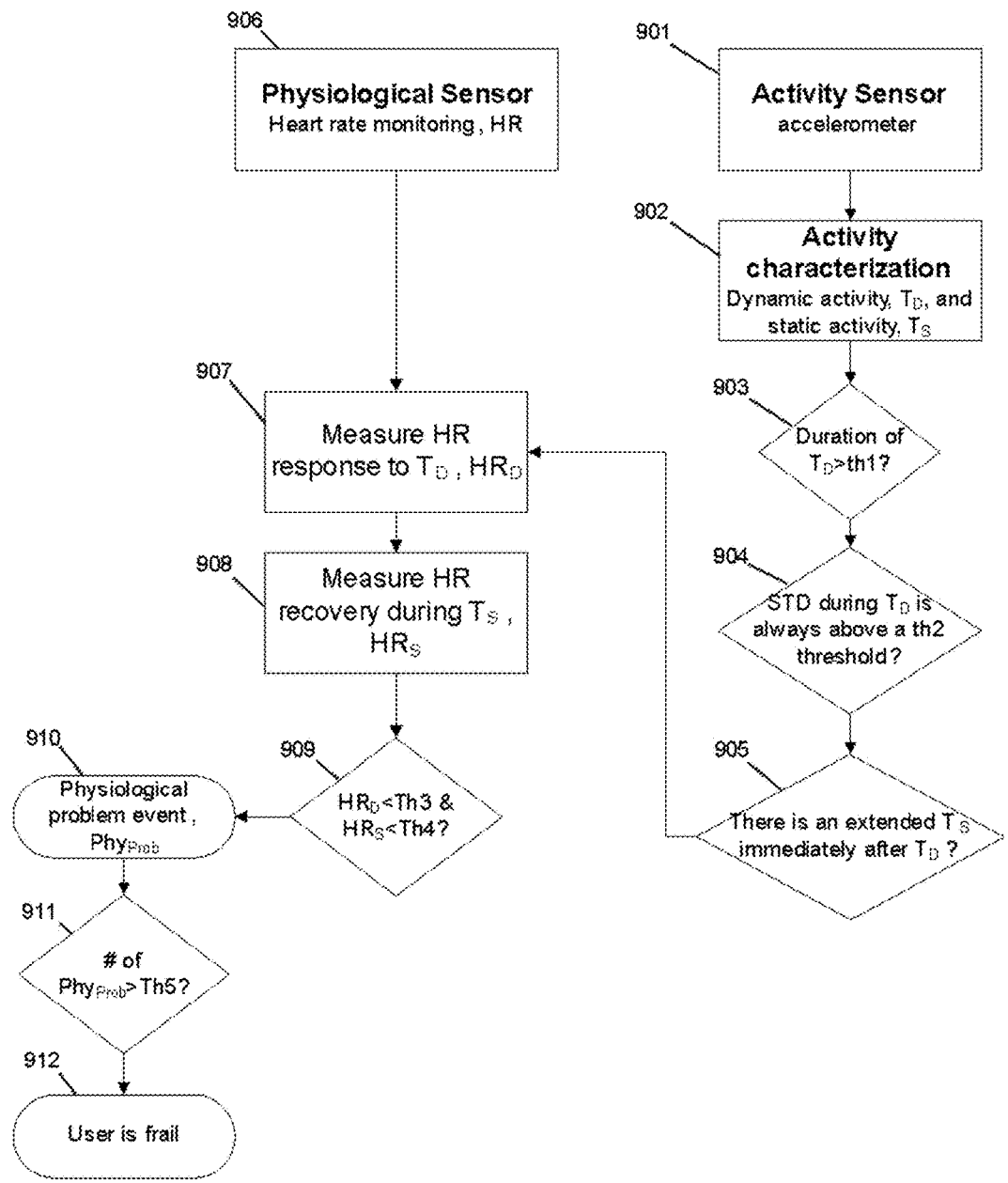
FIG. 9 illustrates methods used to identify failure in physiological response and recovery response to a dynamic activity.

An algorithm which may be employed according to present principles to identify frail subjects has been summarized in the flowchart of FIG. 9. A physiological sensor 906 is employed to measure a physiological parameter, e.g., a heart rate response to a dynamic activity, in step 907, followed by a measurement of a heart rate recovery over a static activity in step 908. In this way, a physiological response problem may be identified by characterization of a heart rate response to a pre-defined dynamic activity with a consistent duration, e.g., the duration of a dynamic activity may be greater than a pre-defined threshold, and the standard deviation of acceleration during each sub-period, e.g., 5 seconds, of this period may also be greater than a pre-defined threshold. These steps are illustrated by steps 901, 902, 903, and 904.

Another criteria which may be employed to determine a dynamic activity of interest is the occurrence of a prolonged static activity with predefined characteristics immediately after the dynamic activity of interest. Examples of said predefined characteristics include, but are not limited to, a duration longer than a pre-defined threshold, and a standard deviation of acceleration during this period (e.g., every 5 seconds) less than a pre-defined threshold. This step corresponds to step 905 in FIG. 9. When a sequence of dynamic and static activities of interest is identified during activities of daily living, the heart rate response is assessed during both detected dynamic and static activities in steps 907 and 908. Some of the characteristics of the heart rate response to a dynamic activity are (but are not limited to) the rate of increase in heart rate from the start of the activity to the time at which the maximum heart rate occurs (e.g., magnitudes 803 and 804), the magnitude of the increase in heart rate in response to the dynamic activity (e.g., magnitudes 807 and 808), and so on. Some of the characteristics of heart rate recovery during the static period immediately after a dynamic period (shaded area 803) are (but are not limited to): the rate of heart rate reduction from the time of occurrence of the maximum heart rate to the time of occurrence of the maximum reduction in heart rate during the static period (e.g., magnitudes 805 and 806), and the magnitude of maximum reduction in heart rate during the static activity (e.g., magnitudes 809 and 810), etc. The dynamic activities of interest are (but are not limited to): SI-ST, ST-SI, cyclic activities, e.g., walking, turning, climbing stairs, high energetic dynamic activities, etc.

A physiological response to a dynamic activity of interest is considered to be a problem response if (1) the magnitude and slope of response to the dynamic activity are lower than a threshold; and (2) recovery during the static period after termination of the dynamic activity is lower than a threshold. These parameters are determined in steps 909 and 910 in FIG. 9. In steps 911 and 912, a subject is identified as frail if the number of identified physiological problems during a defined period (e.g., 24 hours) exceeds a pre-defined threshold. It will be understood that such parameters as given above are purely exemplary and that variations of the same will be apparent to one of ordinary skill in the art given this teaching.

Identification of Open-Loop and Closed-Loop Conditions

Postural instability is associated with frailty syndrome and increased risk of falling. Balance requires open-loop (OL) postural muscle control, and closed-loop (CL) vestibular, visual, proprioceptive and somatosensory cues for regulation of balance. Diminishment in muscle performance increases subject dependency to sensory feedback, i.e., CL strategy, and thus reduces the time interval that the subject may be able to retain an OL postural control strategy. In other words, for a frail individual to ambulate, he/she needs to rely on additional feedback signals, e.g., visual, vestibular, and somatosensory feedback; whereas a non-frail individual may not need these additional inputs (and thus sufficiently function in open loop mode).

Figure 10:
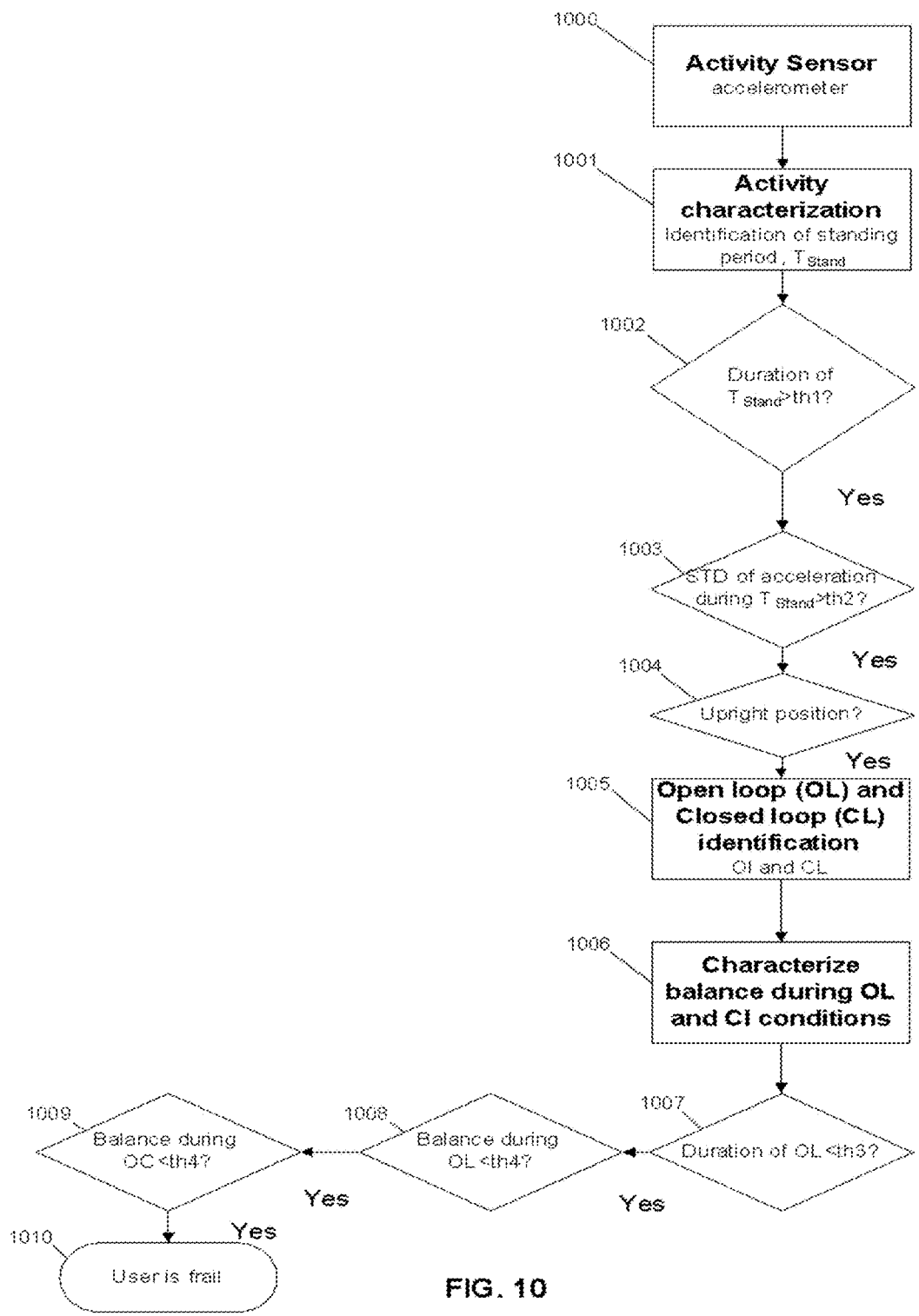
FIG. 10 illustrates methods used to identify postural instability via characterization of balance during standing and further characterization of open loop and closed loop strategies.

Systems and methods according to present principles propose identifying OL and CL postural strategies during activities of daily living and separately characterizing balance during OL and CL. FIG. 10 illustrates one exemplary algorithm as a solution. First, an activity sensor such as an accelerometer 1000 identifies a standing period during activities of daily living ($T_{stand}$) in step 1001. Only those standing periods are considered for OL and CL characterization that are long enough, e.g., with duration greater than 10 seconds, as determined in step 1002, and determined as sufficiently standing, e.g., the standard deviation of acceleration during $T_{stand}$ is lower than a predefined threshold, as determined in step 1003, and the posture is determined as upright, e.g., the absolute value of vertical acceleration is close to one unit of gravity, as determined in step 1004.

In step 1005, the method identifies open-loop and closed-loop strategies. The OL-CL method may be employed along with, or as part of, the systems and methods according to present principles. In summary, body sway during $T_{stand}$ is estimated by measuring the value of body acceleration, body velocity (integration of body acceleration), or body position (integration of body velocity), resulting in $Stand_{Sway}$. The square of displacement $(\Delta r_i)^2$ between successive $Stand_{Sway}$ data points separated in time by a specified time-interval ($\Delta t$) are calculated. The squared displacements $(\Delta r_i)^2$ are then averaged over the specified time-interval ($\Delta t$), ranging from 0 to 10 seconds ($0 \leq \Delta t \leq 10$ sec), to provide a plot of mean square $Stand_{Sway}$ displacement ($\Delta r^2$) versus $\Delta t$ according to the following formula:

$$\langle \Delta r^2 \rangle_{\Delta t} = \frac{\sum_{i=1}^{N-m} (\Delta r_i)^2}{(N-m)}$$

where N is the number of data points for the first 10 seconds of $Stand_{Sway}$ data series, and for a given $\Delta t$, m is the number of data intervals. Using this approach, OL and CL conditions are identified by fitting two best linear fits to $Stand_{Sway}$ displacement ($\Delta r^2$) data. The determined body swaying may then be the basis for step 1006, where the balance of the subject user during open loop and closed loop conditions is characterized.

In step 1010, a subject user is identified to have a poor balance and consequently to be frail if the duration of OL strategy is less than a predefined threshold, as determined in step 1007, and has poor balance during OL and CL, as determined in steps 1008 and 1009. Balance during OL and CL conditions can be characterized by measuring the range of sway, speed of change in sway magnitude, and acceleration change in sway magnitude, e.g., using steps within step 1006.

Combination of Measured Parameters to Classify Frailty

In other implementations, the sensitivity and specificity of frailty classifications can be enhanced even further by employing a combination of parameters described above using a linear combination of factors, e.g., multivariable regression model, or a non-linear, e.g., neural network, model (step 123 in FIG. 1). For example, each of the measured parameters may be scaled to a score of zero to five, where a higher number indicates a higher degree of problem. Then, each parameter may be weighted and combined with other parameters using a linear or non-linear model to identify the final score of frailty. The following equation demonstrates an example of such a combination:

$$\text{Frailty Score} = A1X1 + A2X2 + A3X3 + \ldots + A8X8,$$

where $A1$=flopping score, $A2$=slowness score, $A3$=weakness score, $A4$=exhaustion score, $A5$=physiological response score, $A6$=physiological recovery score, $A7$=activity response to distraction score, and $A8$=postural instability score, and $Xi$ are the weightings.

The final score may be mapped to a scale of zero to five, where a higher number indicates more severity in frailty status. If an additional notion of physiological parameters emerged, those parameters could be added to the classification model described above.

Systems and methods according to present principles not only allow identification of frailty during activities of daily living during unsupervised conditions, such may also be implemented during supervised conditions including in-home, in-laboratory and in-clinic conditions.

EXAMPLES OF USE

Example One

The system was used to evaluate a 74 year old man, who has general functional decline over the last six months. The system evaluated his frailty status, and all parameters were interrogated with the following readout: flopping received a score of 5, slowness received a score of 3, exhaustion received a score of 3, cognitive problems received a score of 0, physiological response received a score of 2, physiological recovery received a score of 4, response to distraction received a score of 0, and balance received a score of 4. The model overall gave a score of 3 and classified the subject as pre-frail.

Example Two

The system was also used to evaluate a 80 year old female, who has chronic lung disease, was a former smoker, and who had multiple history of falls during the previous year. No evidence for cancer or other acute elements were identified. Using the monitor, the following results emerged: flopping received a score of 4; slowness received a score of 5, exhaustion received a score of 5, cognitive problems received a score of 3, physiological response received a score of 5; physiological recovery received a score of 4, response to distraction received a score of 3, and balance received a score of 4. The model overall gave a score of 4.5 and classified the subject as frail.

Using systems and methods according to present principles, a physician or clinician can analyze a frailty of the subject user accurately and effectively. It is further noted that such analysis is generally individualized, computationally-intensive, and is not capable of being performed in the absence of an appropriate computing environment to measure the individual's response to a sufficient number of performance impact variables. By performing the steps described above, and subsequent analysis, the computing environment performing these steps operates in a more efficient manner as the computing environment is able to "home in on" a classification, stratification, or categorization of frailty for a user in a rapid manner.

The system and method may be fully implemented in any number of computing devices. Typically, instructions are laid out on computer readable media, generally non-transitory, and these instructions are sufficient to allow a processor in the computing device to implement the method of the invention. The computer readable medium may be a hard drive or solid state storage having instructions that, when run, are loaded into random access memory. Inputs to the application, e.g., from the plurality of users or from any one user, may be by any number of appropriate computer input devices. For example, users may employ a keyboard, mouse, touchscreen, joystick, trackpad, other pointing device, or any other such computer input device to input data relevant to the calculations. In particular systems and methods according to present principles, data may be input visually via cameras, physiological sensors such as those measuring heart rate, skin conductance, and the like, accelerometers, GPS devices, and the like. Data may also be input by way of an inserted memory chip, hard drive, flash drives, flash memory, optical media, magnetic media, or any other type of file—storing medium. The outputs may be delivered to a user by way of a video graphics card or integrated graphics chipset coupled to a display that maybe seen by a user. Alternatively, a printer may be employed to output hard copies of the results. Given this teaching, any number of other tangible outputs will also be understood to be contemplated by the invention. For example, outputs may be stored on a memory chip, hard drive, flash drives, flash memory, optical media, magnetic media, or any other type of output. It should also be noted that the invention may be implemented on any number of different types of computing devices, e.g., personal computers, laptop computers, notebook computers, net book computers, handheld computers, personal digital assistants, mobile phones, smart phones, tablet computers, and also on devices specifically designed for these purpose. In one implementation, a user of a smart phone or Wi-Fi—connected device downloads a copy of the application to their device from a server using a wireless Internet connection. An appropriate authentication procedure and secure transaction process may provide for payment to be made to the seller. The application may download over the mobile connection, or over the WiFi or other wireless network connection. The application may then be run by the user. Such a networked system may provide a suitable computing environment for an implementation in which a plurality of users provide separate inputs to the system and method. In the below system where frailty monitoring systems are contemplated, the plural inputs may allow plural users to input relevant data at the same time.

While the invention has been described with respect to certain embodiments, it should be clear to one of ordinary skill in the art, given the teachings and disclosures made herein, that the invention is much broader than the embodiments shown. The invention is susceptible to modifications in the methods and materials. Accordingly, the description represents some, but not all, representations, and therefore the scope of this invention is to be limited only by the claims appended to this description.

The invention claimed is:

1. An ambulatory system to identify the presence and degree of frailty comprising:
a wearable sensor, configured to be attached to or worn by a person, the sensor configured to be attached to an upper body of a person, the sensor including at least an accelerometer configured to generate signals in response to motion or movements of the person, the accelerometer configured to measure at least a frontal acceleration pattern; and
one or more processor circuits configured to receive and analyze one or more signals from the accelerometer as a result of spontaneous daily activity, the processor circuits configured to determine information about frailty status including at least a determination that assists in the classification of the person as non-frail, pre-frail, or frail, the one or more processor circuits performing at least the following steps:
determining a score for one or more frailty related biomarkers selected from the group consisting of: flopping, cautious sitting, slowness, weakness, cognitive decline, cautious sit to walk, or exhaustion, the score determined based at least on the measured frontal acceleration pattern measured by the accelerometer, the score further determined based on identifying activities measured by the accelerometer as being dynamic or static;
determining a score for one or more physiological responses to the identified dynamic or static activities, the responses selected from the group consisting of: heart rate, heart rate variability, respiration rate, or skin temperature, the determined score for one or more physiological responses to the identified dynamic or static activities based at least in part on abnormal physiological responses to the identified dynamic or static activities, and
using the determined score for the one or more frailty related biomarkers as determined by the one or more processor circuits analyzing the signals from the accelerometer and the determined score for the one or more physiological responses to calculate an overall score, and from the overall score classifying the person into one of a plurality of predetermined classifications, the predetermined classifications including at least non-frail, pre-frail, or frail, wherein the classifying provides an early identification of early markers of frailty to allow early intervention and rehabilitation as compared to non-ambulatory systems that do not use signals resulting from spontaneous daily activity.

2. The system of claim 1, wherein the information about frailty status is transmitted wireless in real time or at predefined periods of time to a receiver.

3. The system of claim 1, wherein the accelerometer is configured to measure a frontal acceleration pattern, and wherein said one or more processor circuits are further programmed to identify a sit to stand or stand to sit postural transfer based on identifying a dynamic pattern before or after a peak detected in the frontal acceleration pattern.

4. The system of claim 1, wherein the accelerometer is configured to measure vertical accelerations, and wherein said one or more processor circuits are further programmed to: identify the dynamic or the static activity based on a standard deviation of a vertical or a frontal acceleration in a pre-defined interval, including a predefined interval before and after a postural transfer.

5. The system of claim 4, wherein said one or more processor circuits are further programmed to identify a standing posture if a dynamic activity and a static activity are identified immediately after and before a postural transfer, respectively.

6. The system of claim 4, wherein said one or more processor circuits are further programmed to identify a sitting posture if a static activity and a dynamic activity are identified immediately after and before a postural transfer, respectively.

7. The system of claim 4, wherein said one or more processor circuits are further programmed to measure a speed of low intensity movement based on an integration of acceleration during a static activity followed by a removal of drift of integration.

8. The system of claim 4, wherein said one or more processor circuits are further programmed to measure a speed of a high intensity movement based on an integration of acceleration during a dynamic activity followed by a removal of drift of integration.

9. The system of claim 4, wherein said one or more processor circuits are further programmed to identify frailty status by measuring a number of flopping events occurring within a pre-defined interval by identifying a number of immediate transfers from a dynamic activity to a static activity with a transfer speed of greater than a pre-defined threshold.

10. The system of claim 4, wherein said one or more processor circuits are further programmed to identify frailty status by measuring a number of cautious-sitting events occurring within a pre-defined interval by identifying a sequence of a dynamic activity followed by a static activity longer than a pre-defined threshold followed by a postural transfer to sitting or lying.

11. The system of claim 4, wherein said one or more processor circuits are further programmed to identify frailty status by measuring slowness of movement as characterized by a duration or magnitude of acceleration, or a magnitude of velocity, during a postural transfer or a dynamic activity.

12. The system of claim 4, wherein said one or more processor circuits are further programmed to identify frailty status by measuring weakness as characterized by a standard deviation of a frontal or a vertical acceleration or a magnitude of speed during a dynamic activity.

13. The system of claim 1, wherein said one or more processor circuits are further programmed to identify frailty status by measuring exhaustion based on measurement of a rate of change and a total change in speed or acceleration of movement during cyclic activities, consecutive sit to stand postural transfers, or consecutive body joint flexions and extensions.

14. The system of claim 1, wherein said one or more processor circuits are further programmed to identify frailty status by measuring non-uniformity of step-to-step walking speed.

15. The system of claim 1, further comprising a sensor to measure heart rate or an electrocardiogram.

16. The system of claim 15, wherein said one or more processor circuits are further programmed to identify, confirm and define frailty status based on measuring one or more of a rate of change of heart rate or heart rate variability, and a magnitude of change in heart rate or heart rate variability during a transition from a static activity to a dynamic activity.

17. The system of claim 15, wherein said one or more processor circuits are further programmed to identify frailty status based on measuring one or more of a rate of change of heart rate, a magnitude of change in heart rate, and a change of heart rate variability during a transition from a dynamic activity to a static activity.

18. The system of claim 15, wherein said one or more processor circuits are further programmed to identify frailty status based on measuring a duration or a number or premature junctional contractions (PJC) episodes during a predefined time interval.

19. The system of claim 1, further comprising a sensor to measure respiration rate.

20. The system of claim 19, wherein said one or more processor circuits are further programmed to identify frailty status based on measuring one or more of a rate and magnitude of change in respiration rate from a static activity to a dynamic activity.

21. The system of claim 19, wherein said one or more processor circuits are further programmed to identify frailty status based on measuring one or more of a rate and magnitude of change in respiration rate from a dynamic activity to a static activity.

22. The system of claim 1, further comprising a sensor to measure audio.

23. The system of claim 22, wherein said one or more processor circuits are further programmed to identify whether the person is talking based on measuring one or more of a frequency of audio, a magnitude of audio, a change in upper body acceleration, or a change in respiration rate.

24. The system of claim 22, wherein said one or more processor circuits are further programmed to measure a difference in one or more of the following parameters of gait between when the person is talking and when the person is not talking: speed, cadence, or step-to-step variation in step duration.

25. The system of claim 22, wherein said one or more processor circuits are further programmed to identify frailty status based said differences in one or more parameters of gait between when the user is talking and when the user is not talking.

26. The system of claim 1, wherein said one or more processor circuits are further programmed to measure body sway based on measurements of acceleration and speed during a standing posture.

27. The system of claim 26, wherein said one or more processor circuits are further programmed to identify frailty status by characterization of body sway during open-loop and closed-loop conditions.

28. The system of claim 26, wherein said one or more processor circuits are further programmed to identify open-loop and closed-loop conditions by measuring a body sway.

29. The system of claim 1, wherein said one or more processor circuits are further programmed to identify frailty status by a linear or non-linear combination of two or more parameters.

30. The system of claim 1, wherein the sensor is further configured to measure a vertical acceleration signal.

31. The method of claim 1, wherein the spontaneous daily physical activity is unsupervised activity.

32. An ambulatory method for categorizing frailty status of a person, comprising:

receiving one or more signals from an accelerometer, the accelerometer attached to an upper body of a person, the one or more signals including at least one acceleration signal in response to motion or movements of a person as a result of spontaneous daily activity, the signals measuring at least a frontal acceleration pattern; and determining information about frailty status including at least a determination that classifies the person as non-frail, pre-frail, or frail, wherein the determining information is performed by the following steps:

determining a score for one or more frailty related biomarkers selected from the group consisting of: flopping, cautious sitting, slowness, weakness, cognitive decline, cautious sit to walk, or exhaustion, the score determined based at least on the measured frontal acceleration pattern measured by the accelerometer, the score further determined based on identifying activities measured by the accelerometer as being dynamic or static;

determining a score for one or more physiological responses to the identified dynamic or static activities, the responses selected from the group consisting of: heart rate, heart rate variability, respiration rate, or skin temperature, the determined score for one or more physiological responses to the identified dynamic or static activities based at least in part on abnormal physiological responses to the identified dynamic or static activities, and using the determined score for the one or more frailty related biomarkers and the score for the one or more physiological responses to the identified dynamic or static activities to calculate an overall score, and from the overall score classifying the person into one of a plurality of predetermined classifications, the predetermined classifications including at least non-frail, pre-frail, or frail, wherein the classifying provides an early identification of early markers of frailty to allow early intervention and rehabilitation as compared to non-ambulatory systems that do not use signals resulting from spontaneous daily activity.

33. The method of claim 32, wherein the acceleration signal is a frontal acceleration signal, and further comprising identifying a sit to stand or stand to sit postural transfer based on identifying a dynamic pattern before or after a peak detected in the frontal acceleration pattern.

34. The method of claim 33, wherein the acceleration signal is a vertical acceleration signal, and further comprising identifying the dynamic and a static activity based on a standard deviation of a vertical or a frontal acceleration in a predefined interval, including a predefined interval before or after a postural transfer.

35. The method of claim 34, further comprising identifying frailty status by measuring weakness as characterized by a standard deviation of a frontal or a vertical acceleration or a magnitude of speed during a dynamic activity.

36. The method of claim 32, further comprising identifying frailty status by measuring exhaustion based on measurement of a rate of change and a total change in speed or acceleration of movement during cyclic activities, consecutive sit to stand postural transfers, or consecutive body joint flexions and extensions.

37. The method of claim 32, further comprising identifying frailty status by measuring non-uniformity of step-to-step walking speed.

38. The method of claim 32, further comprising identifying, confirming and defining frailty status based on measuring one or more of a rate of change of heart rate or heart rate variability, and a magnitude of change in heart rate or heart rate variability during a transition between a static activity and a dynamic activity.

39. The method of claim 32, further comprising identifying frailty status based on measuring one or more of a rate and magnitude of change in respiration rate between a static activity and a dynamic activity.

* * * * *